US011457909B2

(12) United States Patent
Jung

(10) Patent No.: US 11,457,909 B2
(45) Date of Patent: Oct. 4, 2022

(54) SHEATH DEVICE FOR BIPORTAL ENDOSCOPIC SPINAL SURGERY

(71) Applicants: ENDOVISION CO., LTD., Daegu (KR); Min Ho Jung, Daegu (KR)

(72) Inventor: Min Ho Jung, Daegu (KR)

(73) Assignees: Min Ho Jung; ENDOVISION CO., LTD.

( * ) Notice: Subject to any disclaimer, the term of this patent is extended or adjusted under 35 U.S.C. 154(b) by 0 days.

(21) Appl. No.: 16/763,175

(22) PCT Filed: Nov. 30, 2017

(86) PCT No.: PCT/KR2017/013881
§ 371 (c)(1),
(2) Date: May 11, 2020

(87) PCT Pub. No.: WO2019/098444
PCT Pub. Date: May 23, 2019

(65) Prior Publication Data
US 2020/0383675 A1    Dec. 10, 2020

(30) Foreign Application Priority Data

Nov. 14, 2017 (KR) .......................... 10-2017-0151636
Nov. 30, 2017 (KR) .......................... 10-2017-0162530

(51) Int. Cl.
*A61B 17/02* (2006.01)
*A61B 1/31* (2006.01)
*A61B 17/34* (2006.01)

(52) U.S. Cl.
CPC ...... *A61B 17/0218* (2013.01); *A61B 17/3496* (2013.01); *A61B 17/3498* (2013.01); *A61B 2017/0256* (2013.01); *A61B 2217/007* (2013.01)

(58) Field of Classification Search
CPC .......................... A61B 17/0218; A61B 1/3135
See application file for complete search history.

(56) References Cited

U.S. PATENT DOCUMENTS 3,598,108 A * 8/1971 Jamshidi ............ A61B 10/0233
600/567
4,261,346 A * 4/1981 Wettermann ........... A61B 1/313
600/104

(Continued)

FOREIGN PATENT DOCUMENTS

| JP | 3429536 B2 | 7/2003 |
| JP | 3834370 B2 | 10/2006 |

(Continued)

OTHER PUBLICATIONS

International Search Report for corresponding International application No. PCT/KR2017/013881; dated Aug. 10, 2018; Machine Translation (5 pages).

*Primary Examiner* — Nicholas W Woodall
(74) *Attorney, Agent, or Firm* — Mendelsohn Dunleavy, P.C.

(57) ABSTRACT

An endoscopic device for biportal endoscopic spinal surgery is proposed. The device includes: a guide tube as a hollow tubular member extending in a longitudinal direction and having a front end thereof reaching a target site in a patient's body when being used, the guide tube accommodating a probe of an endoscope inserted therein; a saline solution guide part mounted on a rear end of the guide tube and guiding a saline solution injected from an outside to an inside of the guide tube; and an adapter part positioned at the rear end of the guide tube and guiding the probe of the endoscope to use to the guide tube.

7 Claims, 12 Drawing Sheets

(56) References Cited

U.S. PATENT DOCUMENTS

| | | | | |
|---|---|---|---|---|
| 4,973,321 | A * | 11/1990 | Michelson | A61B 1/00094 |
| | | | | 600/114 |
| 5,156,142 | A * | 10/1992 | Anapliotis | A61B 1/00135 |
| | | | | 600/156 |
| 5,651,783 | A * | 7/1997 | Reynard | A61B 1/042 |
| | | | | 606/17 |
| 6,402,715 | B2 * | 6/2002 | Manhes | A61B 1/00135 |
| | | | | 600/156 |
| D596,291 | S * | 7/2009 | Berberich | D24/133 |
| 9,700,378 | B2 | 7/2017 | Mowlai-Ashtiani | |
| 2004/0225192 | A1 * | 11/2004 | Young | A61B 17/3423 |
| | | | | 600/204 |
| 2016/0120395 | A1 * | 5/2016 | Qi | A61B 1/00135 |
| | | | | 600/123 |
| 2020/0187983 | A1 * | 6/2020 | Dejima | A61B 1/00091 |

FOREIGN PATENT DOCUMENTS

| | | |
|---|---|---|
| JP | 2013-138790 A | 7/2013 |
| JP | 2016-522707 A | 8/2016 |

* cited by examiner

SHEATH DEVICE FOR BIPORTAL ENDOSCOPIC SPINAL SURGERY

TECHNICAL FIELD

The present invention relates to minimally invasive biportal endoscopic spinal surgery (i.e., Unilateral Biportal Endoscopy, UBE) and, more particularly, to a sheath device for biportal endoscopic spinal surgery that maintains a continuous and smooth supply of a saline solution to a surgical site in a patient's body, thereby securing excellent visibility of the surgical site to greatly improve a success rate of the surgery.

BACKGROUND ART

The human spine consists of seven cervical vertebrae constituting the neck, twelve thoracic vertebrae constituting the backbone, five lumbar vertebrae constituting the lumbar spine, the sacrum in which five sacral vertebrae constituting the hipbone are fused to form a single bone, and the coccyx in which four coccygeal vertebrae constituting the tailbone are fused to form a single bone. These vertebrae are interconnected by the vertebral joints, and the intervertebral disc is formed between each vertebral joint. The spine having the above structure not only supports posture, but also plays an important role in protecting the internal organs.

However, when an intervertebral disc of the spine is denatured or ruptured and thus departs from a normal position, when a vertebral joint composed of protrusions at the rear of the spine is damaged or denatured, or when the spine is deformed and displaced from the normal position, the nerve passing through the spinal canal is compressed, thereby causing back pain.

Meanwhile, an incision that has been conventionally performed as a surgical method for an operation related to a spine having various symptoms has a disadvantage in that important spinal muscles are damaged and the recovery period is prolonged.

Due to these problems, recently, a surgical method called percutaneous endoscopic interlaminar decompression, which is a minimally invasive spine surgery using an endoscope, is also performed. However, the percutaneous endoscopic interlaminar decompression itself is a surgery having a significantly higher degree of difficulty, and in particular, despite the use of a microscope or a spinal endoscope as an auxiliary device, difficulties may occur due to poor visibility.

Compared to percutaneous uniportal interlaminar epidural endoscopic surgery, the recent endoscopic surgical technique of percutaneous biportal endoscopic decompression has an advantage in that muscle damage may be reduced and it is easy to observe the transverse muscle in a deep position, as an example, because of good visibility.

Percutaneous biportal endoscopic decompression, also called biportal endoscopic spinal surgery, may secure clear visibility of a surgical site compared to that of conventional uniportal endoscopic decompression, thereby enabling various technical difficulties to be solved.

However, since biportal endoscopic spinal surgery uses a surgery method different from that of uniportal endoscopic decompression, required surgical instruments also different. However, the surgical instruments for biportal endoscopic spinal surgery have not yet been developed.

Korean Patent No. 10-1744459 discloses "SURGICAL INSTRUMENT SET TO PERFORM THE POSTERIOR BIPORTAL ENDOSCOPIC SPINAL SURGERY", but only a few surgical instruments are disclosed, and there is no disclosure about a particular surgical device for securing clear visibility during biportal endoscopic spinal surgery.

DISCLOSURE

Technical Problem

The present invention has been devised to solve the above problems, and an objective of the present invention is to provide a sheath device for biportal endoscopic spinal surgery, wherein it is possible to continuously and smoothly supply a saline solution to a surgical site in a patient's body during surgery and also possible to clean the lens of an endoscope with the saline solution, whereby best visibility is guaranteed.

Technical Solution

A sheath device for biportal endoscopic spinal surgery of the present invention for achieving the above objective includes: a guide tube as a hollow tubular member extending in a longitudinal direction thereof and having a front end thereof reaching a target site in a patient's body when being used, the guide tube accommodating a probe of an endoscope inserted therein; a saline solution guide part mounted on a rear end of the guide tube and guiding a saline solution injected from an outside to an inside of the guide tube; and an adapter part positioned at the rear end of the guide tube and guiding the probe of the endoscope to use to the guide tube.

In addition, the saline solution guide part may include: a valve body making the saline solution that is flowed in through an inlet to be passed through and moved to the guide tube; and a volume control valve mounted on the valve body and controlling a flow rate of the saline solution passing through the valve body.

In addition, a damping chamber to receive and accommodate the saline solution that has passed through the valve body and to guide the saline solution to the guide part may be provided between the valve body and the guide tube.

In addition, one or more of the valve bodies may be mounted around the damping chamber to increase an amount of the saline solution supplied to the damping chamber.

In addition, on an inner circumference surface of the guide tube, a guide groove guiding the saline solution in the longitudinal direction of the guide tube, which is flowed into the inside of the guide tube may be formed.

In addition, a plurality of the guide grooves may be disposed in parallel in a circumferential direction of the inner circumference surface of the guide tube, and a linear protrusion contacting the probe of the endoscope and supporting the probe thereof may be provided between each of the guide grooves.

In addition, the adapter part may be provided with a holder maintaining a fixation state of the endoscope to the sheath device.

In addition, at the front end of the guide tube, protrusion parts and recessed parts may be repeatedly formed in a wave pattern along the circumferential direction of the guide tube, thus guiding the saline solution discharged from the guide tube to flow out in a radial direction of the guide tube.

In addition, a side slit to discharge the saline solution discharged from the guide tube in one direction of the guide tube may be formed at a side of the front end of the guide tube.

Advantageous Effects

In a sheath device for biportal endoscopic spinal surgery of the present invention implemented as described above, continuous and smooth supply of a saline solution to a surgical site during surgery is possible and best visibility is also secured by cleaning of a lens with the saline solution, thereby significantly increasing the success rate of surgery.

MODE FOR INVENTION

Hereinafter, an exemplary embodiment according to the present invention will be described in more detail with reference to the accompanying drawings.

Figure 1:
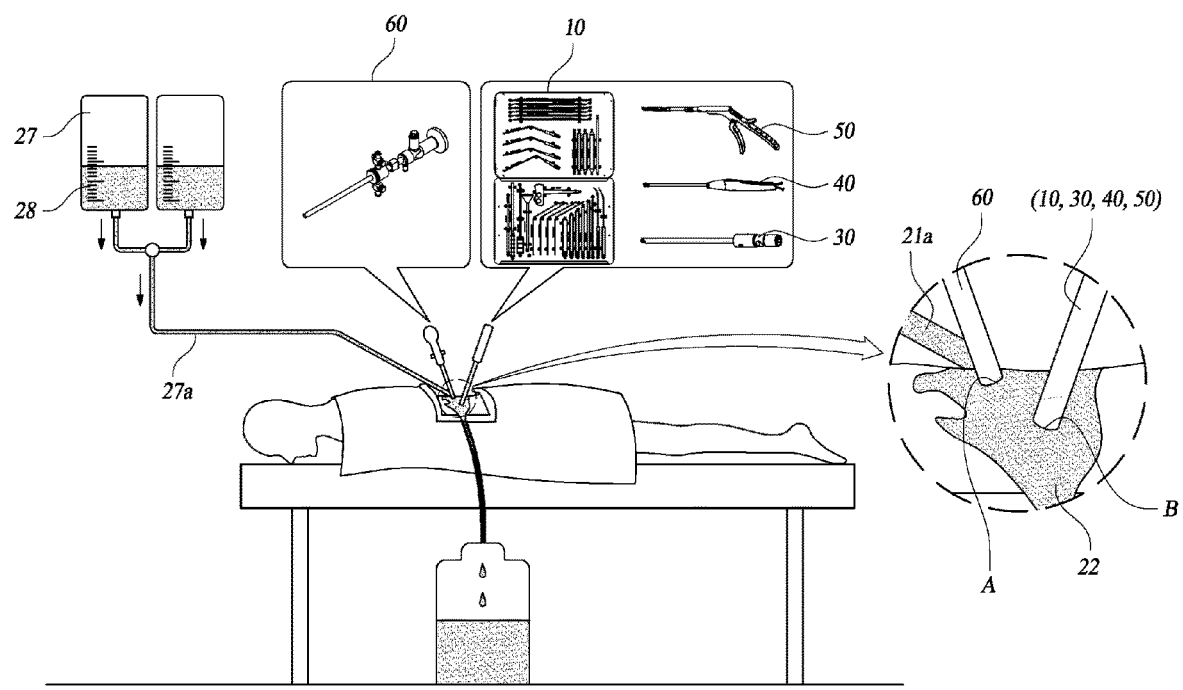
FIG. 1 is a view showing a basic concept of biportal endoscopic spinal surgery.

FIG. 1 is a view for explaining a basic concept of biportal endoscopic spinal surgery.

Fundamentally, biportal endoscopic spinal surgery is a surgery wherein two holes on a target surgical site are perforated, that is, an operation hole B and an endoscope hole A are perforated; a surgical instrument set 10 described above, a radio frequency probe 30, a shaver device 40, or a K-punch 50 is inserted into the operation hole B to treat the target surgical site; and an endoscopic device 60 is inserted into the endoscope hole A to perform the surgery.

In particular, by injecting a saline solution 28 through the endoscopic device 60, the saline solution is guided to flow through the surgical site, whereby the saline solution washes away debris from the surgical site. The used saline solution is discharged from a patient's body through the operation hole B. As will be described later, the endoscopic device 60 according to the present exemplary embodiment serves as a function of supplying the saline solution to the patient's body, in addition to a function of visually identifying the surgical site in the patient's body.

In the biportal endoscopic spinal surgery, since the surgical instruments and the endoscope approach the surgical site through mutually different passages, it is easier to secure visibility than that of the conventional surgical method that forms a single incised hole. Securing of the visibility is an essential factor in spinal surgery.

Meanwhile, since the biportal endoscopic spinal surgery does not share the hole through which the surgical instruments pass with the endoscope, movement is relatively free, thereby enabling more efficient surgery.

The surgical instrument has a wide variety of types, and includes the surgical instrument set 10, the endoscopic device 60, the shaver device 40, the radio frequency probe 30, and the K-punch 50.

Figure 2:
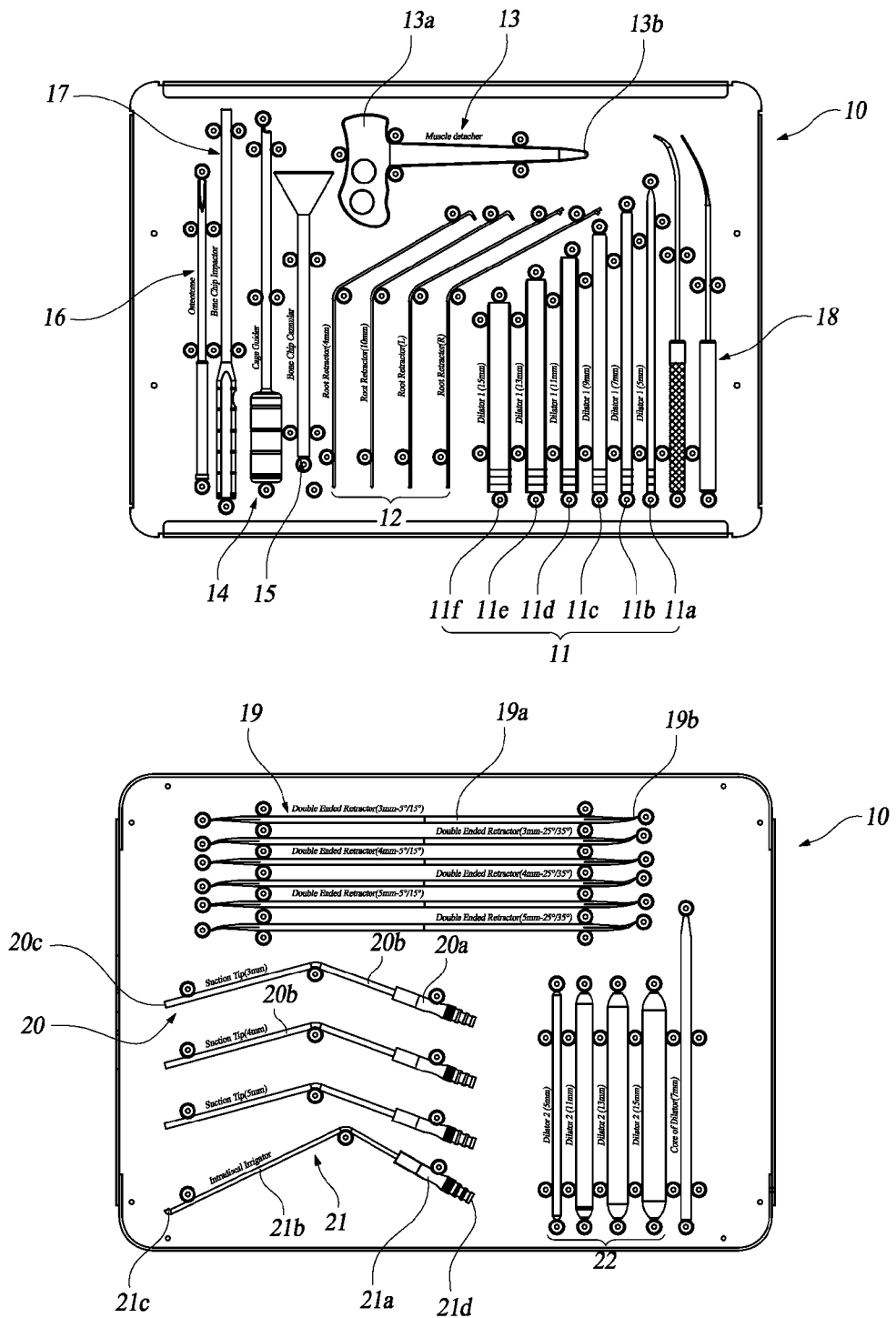
FIG. 2 is a view showing a surgical instrument set that may be used in surgery shown in FIG. 1 as an example.
Figure 3A:
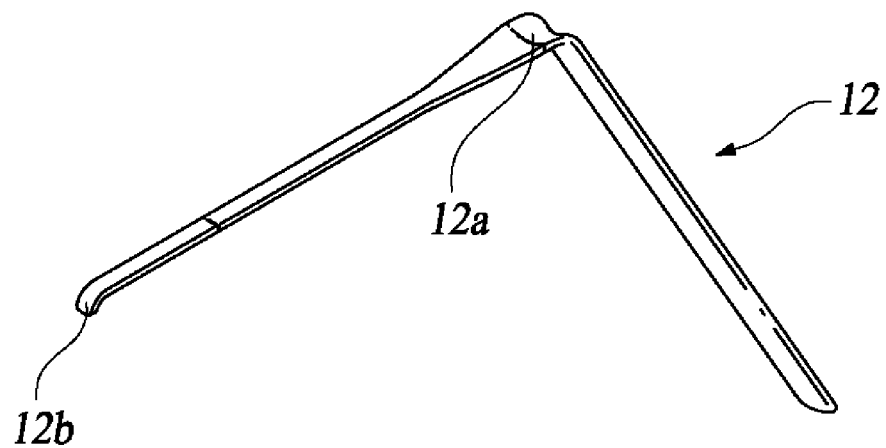
FIGS. 3A to 3D are perspective views showing a muscle retractor shown in FIG. 2.
Figure 3B:
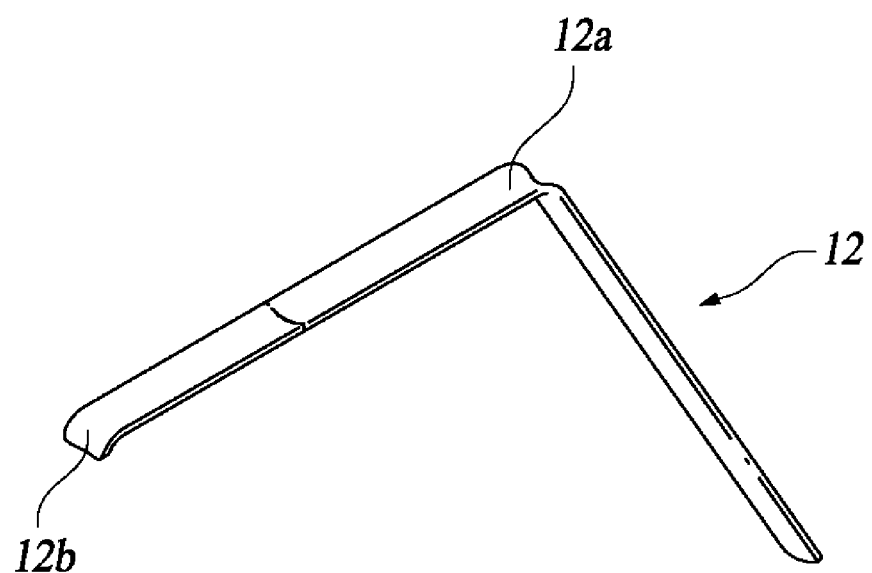
Figure 3C:
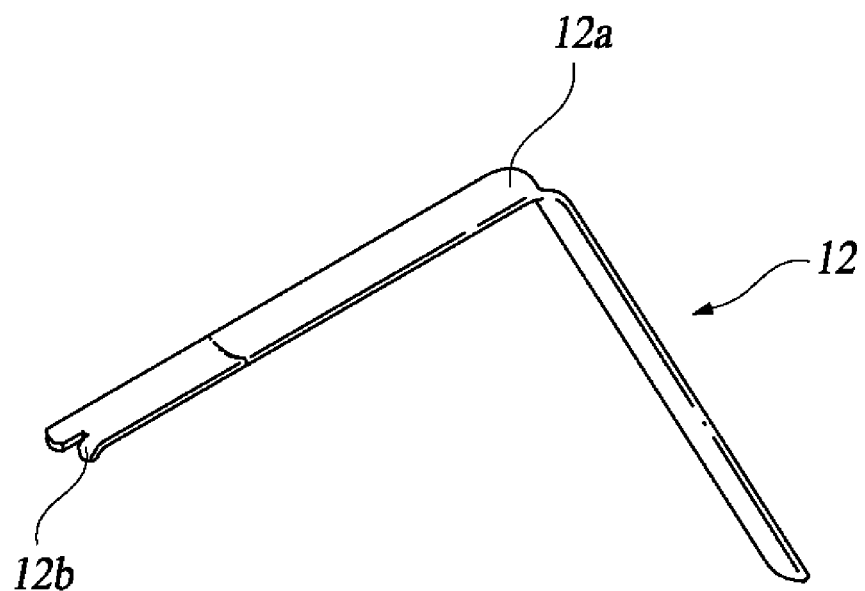
Figure 3D:
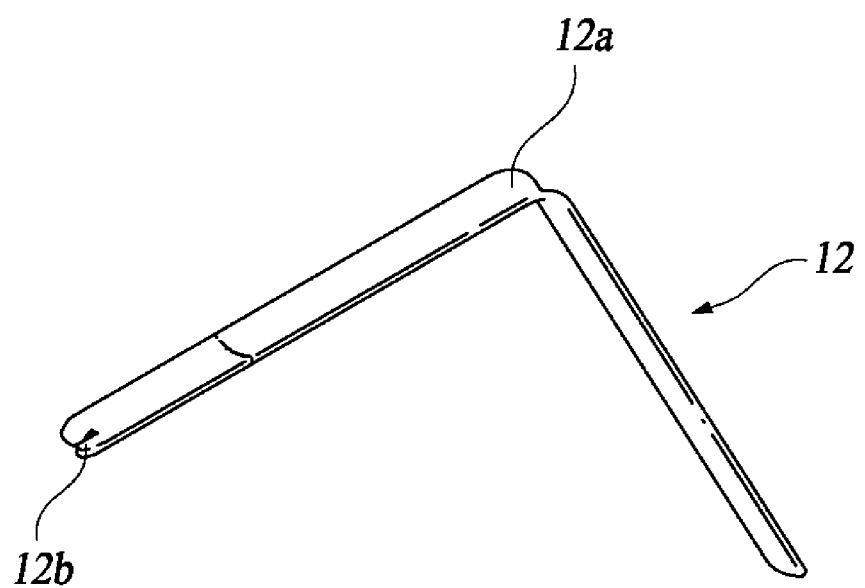
Figure 4:
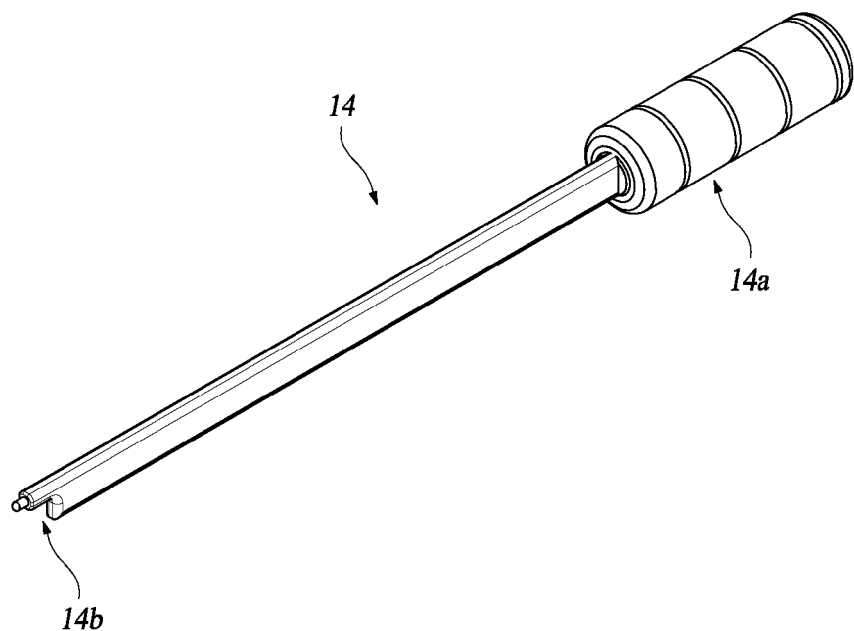
FIG. 4 is a perspective view of a cage guider in FIG. 2.
Figure 5:
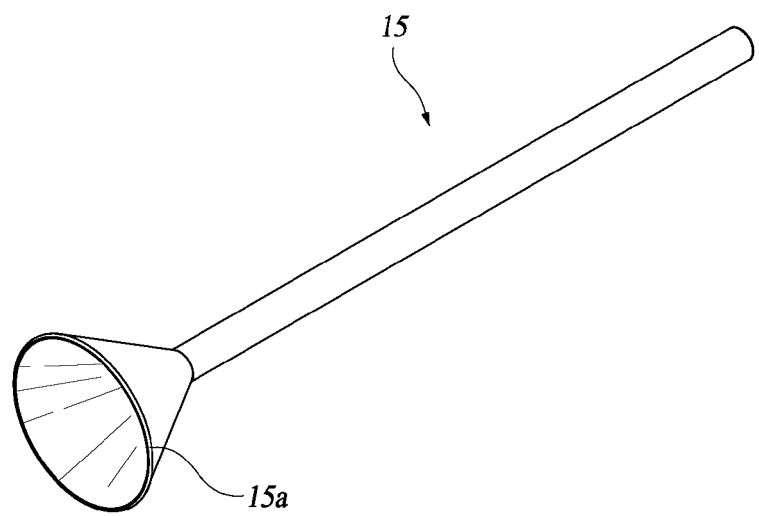
FIG. 5 is a perspective view of a bone chip cannula shown in FIG. 2.
Figure 6:
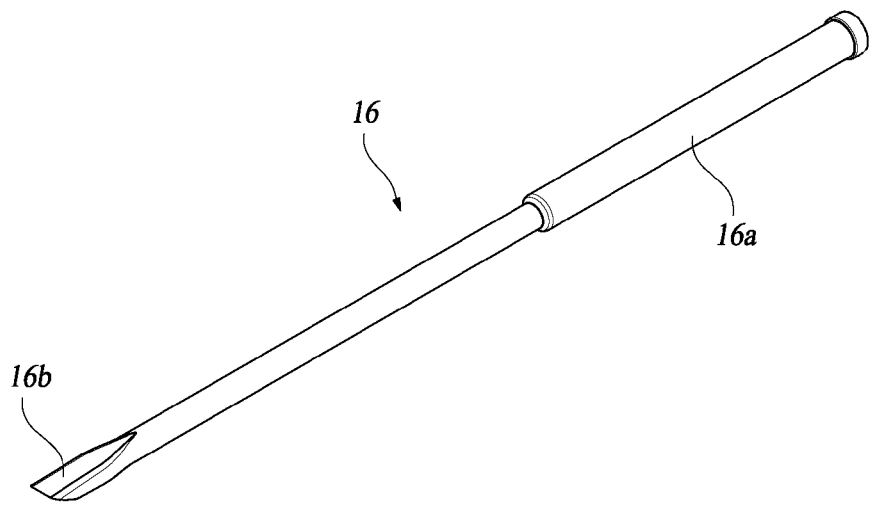
FIG. 6 is a perspective view of an osteotome shown in FIG. 2.
Figure 7:
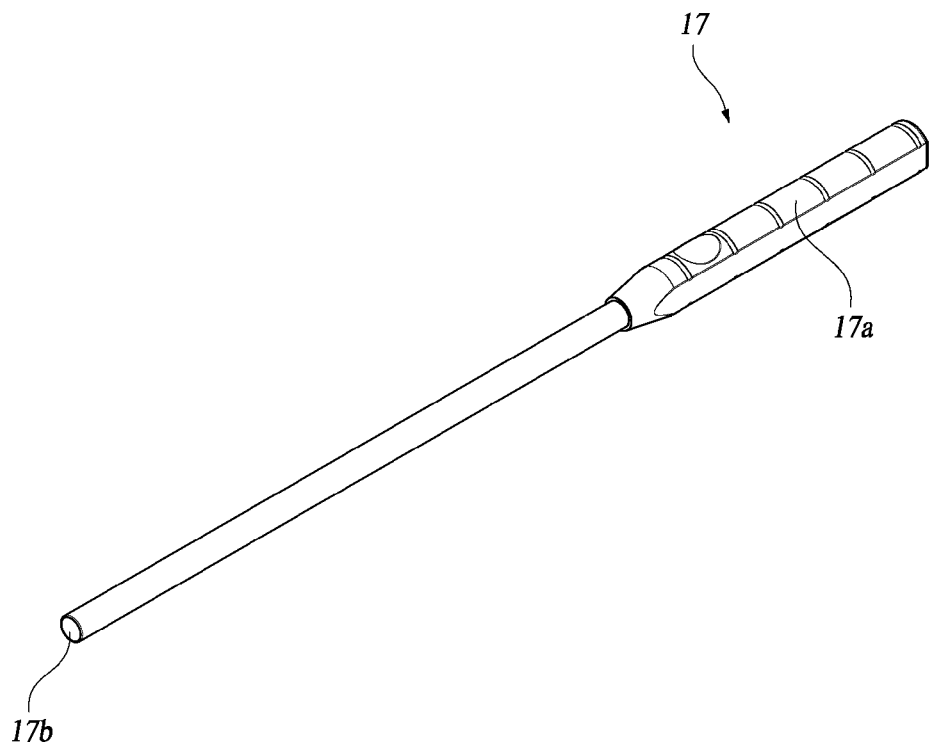
FIG. 7 is a perspective view of a bone chip impactor shown in FIG. 2.
Figure 8:
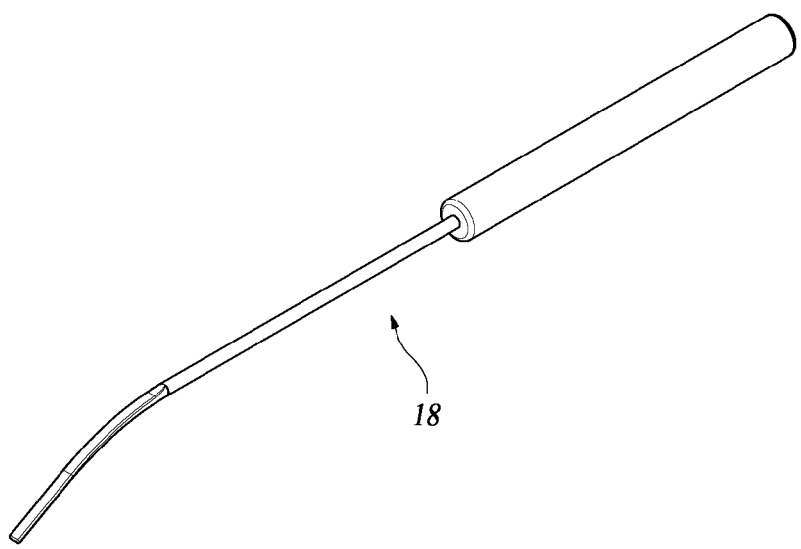
FIG. 8 is a perspective view of a curved remover shown in FIG. 2.

FIG. 2 is a view showing the surgical instrument set 10 that may be used in the surgery shown in FIG. 1, and FIGS. 3A to 3D are perspective views showing a muscle retractor shown in FIG. 2. In addition, FIGS. 4 to 15 are views showing almost all surgical instruments shown in FIG. 1 for reference.

As shown in the drawings, the surgical instrument set 10 includes an expansion tube 11 for expanding a size of the operation hole B and an operation hole retainer 22 for maintaining the expanded operation hole B.

The expansion tubes 11 are instruments for expanding an operation hole into which the instruments are sequentially inserted by size, in order to secure a space for enabling other surgical instruments to access to the operation hole formed on a surgical site during the biportal endoscopic spinal surgery. In other words, after incising the skin to a minimum size with a surgical knife and the like, the expansion tubes 11 are inserted step by step to gradually expand the operation hole.

The expansion tube 11, as shown in FIG. 2, has the form of a tube, with a cavity therein, having a different diameter and length. The expansion tube has an inner diameter of 3 mm and an outer diameter of 5 mm, and each of the inner diameter and outer diameter is increased by 2 mm, and six types of the expansion tube from a first expansion tube 11a to a sixth expansion tube 11f are provided. The first to sixth expansion tubes 11 are selectively used as needed. A scale (not shown) indicating the depth of the expansion tube inserted into the operation hole may be marked on the outer circumference surface of the expansion tube 11.

In addition, the operation hole retainer 22 is a rod-shaped instrument that is inserted into the operation hole to maintain the operation hole secured by the expansion tube 11 and to protect the nerve. The diameter of the operation hole retainer corresponds to the diameter of the expansion tube.

The surgical instrument set 10 further includes a muscle separator 13, a bilateral retractor 19, a muscle retractor 12, a suction tip 20, an intra disc cleaner 21, a cage guider 14, a bone chip cannula 15, an osteotome 16, a bone chip impactor 17, a curved remover 18, and the like.

The muscle separator 13 is an instrument that separates bones and muscles of a target surgical site in a state being inserted into an incision part, which is ensured, so as to secure an entry path, for instruments to be used in subsequent surgery, and a surgical space. That is, the muscle separator is inserted between the layers of the micro muscles, instead of muscle amputation. The muscle separator 13 is composed of a blade part 13b and a handle part 13a. Here, the blade part 13b has a streamlined shape to maximally reduce a wound on a surgical site.

The bilateral retractor 19 is inserted between the surgical spaces formed by the muscle separator 13, and is an instrument used to exfoliate the nerve roots from bones or the yellow ligaments, or to exfoliate muscles or ligaments.

In the bilateral retractor 19, by varying the angle of a tip part 19b formed at both ends thereof, the bilateral retractor is suitable for exfoliating and removing dangerous elements near the nerve, or for applying bone wax to a bleeding point during bone bleeding. The angle of the tip part 19b is 5 to 35 degrees, and the width thereof is 4 mm, 3 mm, 2 mm, and the like. The angle and width of the tip part 19b may vary as much as possible.

In addition, a handle part 19a is positioned at the center of the bilateral retractor 19. The handle part 19a may be provided with a recessed groove for preventing fingers of a user from slipping, or with a certain pattern of irregularities to increase friction.

The muscle retractor 12 is an instrument used to secure a surgical space and constant water pressure in the surgical space by pulling muscles and to guide a path for inserting and removing the surgical instruments, and as shown in FIGS. 3A to 3D, is provided with a first bent part 12a formed at the center thereof and a second bent part 12b formed at one end thereof.

The size of an internal bending angle of the first bent part 12a is about 120 degrees, which is an ideal angle in terms of ergonomics and kinematics when a surgical instrument is inserted and in terms of a lesion when a surgical instrument is inserted. In addition, the outer part of the first bent part 12a has a concave semi-tubular shape, and the second bent part 12b has a shape bent in the same direction as the direction of the first bent part 12a or a half-bent shape so that the muscles and the nerve roots are fixed.

Here, the opposite side surface formed in a semi-tubular shape may serve to guide a path in which a surgical instrument and the like, for chipping or inserting a disc or for tearing off soft tissue such as a ligament, are inserted or removed.

Since the width of a muscle retractor 12 may be variously configured to be 4 mm or 10 mm, etc., it is possible to select and use the muscle retractor having a suitable size according to a surgical site. The muscle retractor helps the operation hole to be opened and closed and maintains the surgical space and the water pressure, thereby enabling a surgeon to check a clear image of the surgical site. In addition, by controlling pressurization and depressurization of the nerve roots, smooth surgery, without damaging to the nerve roots, is allowed to be performed.

In addition, the suction tip 20 is an instrument for suctioning and removing blood, a saline solution (which is being injected for surgery), or soft tissue as well as generated debris in tissue during surgery. During the biportal endoscopic spinal surgery, since constant pressure needs to be applied to a patient's body, the suction tip 20 is used to maintain the constant pressure (e.g., 30 to 50 mmHg). Through the suction tip 20, poor visibility due to debris of bones and soft tissue and the like during surgery may be eliminated.

The suction tip 20 is composed of a handle part 20a to which an outlet is connected, and a suction tube part 20b having a bent shape and provided with a suction hole 20c formed at a front end thereof. The angle of the suction tube part 20b is about 130 to 150 degrees, and the diameter thereof may be implemented to be 3 mm to 5 mm and the like.

The intra disc cleaner 21 is an instrument used to remove debris and the like after making a space for inserting an artificial disk into the disk space. That is, before and after the insertion of the artificial disc, the surrounding debris is discharged, so as not to remain in a patient's body. By using the intra disc cleaner 21, visibility may be sufficiently secured, and an area for cleaning may be accurately identified, thereby allowing quick cleaning and saving of the cleaning water.

The intra disc cleaner 21 includes: a handle part 21a in which a cleaning water inlet 21d is formed; and a water tube part 21b bent at an appropriate angle to secure a user's visibility, and provided with a discharge hole 21c formed at the front end thereof. The bending angle of the water tube part 21b is about 111 degrees to 130 degrees. When the bending angle is 111 degrees or less, the user's visibility is obscured. In addition, when the bending angle is 130 degrees or more, the user's line of vision should be lowered to see the discharge hole 21c.

The cage guider 14, the bone chip cannula 15, the osteotome 16, and the bone chip impactor 17 are instruments used to insert the artificial disk into the disk space.

The cage guider 14 is an instrument used to seat a cage (not shown) in the disk space. A carrying part 14b on which the cage may be placed is formed at one end of the cage guider 14, and a handle part 14a is formed at the other end thereof.

In addition, the bone chip cannula 15 is an instrument used to collect pieces of bone and to insert the same into the disk space. A collection part 15a having a funnel shape is provided at one end of the bone chip cannula 15, and pieces of bone are collected using the collection part 15a.

The osteotome 16 is an instrument used to cut unnecessary bones during surgery. The cutting knife part 16b for cutting the bones is formed at the front end of the osteotome 16. It is apparent that a handle 17a is positioned on the opposite side thereof.

The bone chip impactor 17 is an instrument by which impact is applied in order to accurately seat the artificial disk or the collected pieces of bone, which are inserted in the disk space. At the front end of the bone chip impactor 17 is positioned a tip part 17b to be in contact with objects to be hit, and the opposite side thereof is provided with a handle part 17a.

In addition, the curved remover 18 is an instrument for removing the end plate between the vertebra and the disc, and is bent at the front end thereof to be the shape of a hook. Since one end of the curved remover is formed in the hook shape, it is possible to easily access and remove the end plate positioned between the vertebra and the disc.

Meanwhile, the endoscopic device 60 includes: an endoscope 63 for use in surgery; and a sheath device 61 that receives the endoscope 63 inside thereof and supports the same.

Figure 9:
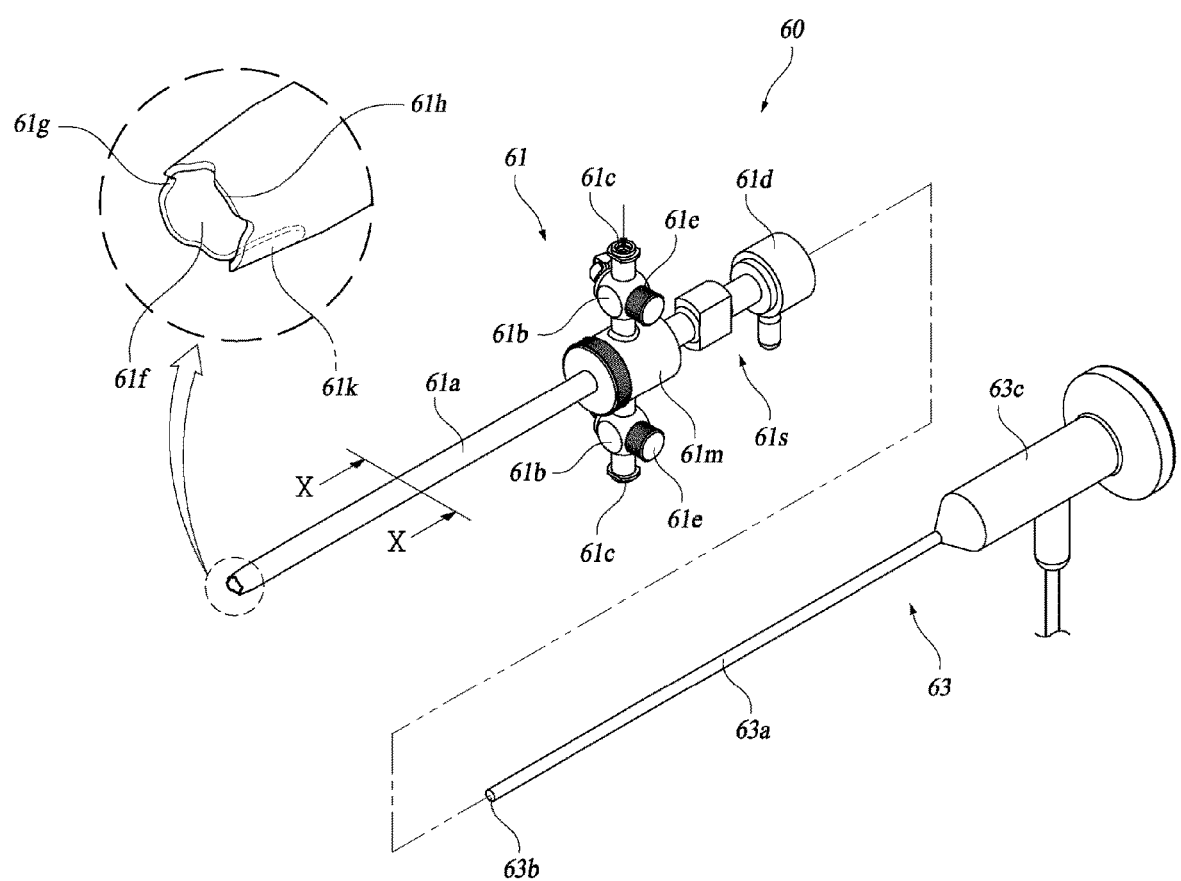
FIG. 9 is an exploded perspective view of an endoscopic device shown in FIG. 1.
Figure 10:
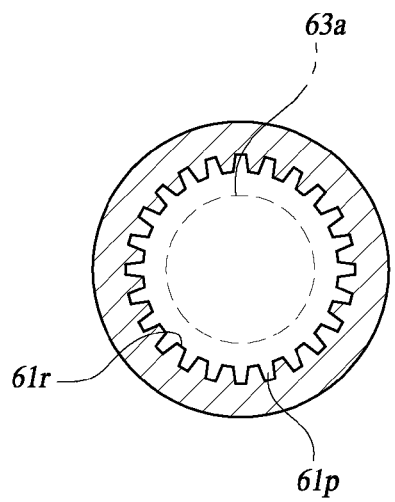
FIG. 10 is a cross-sectional view taken along the line X-X in FIG. 9.
Figure 11:
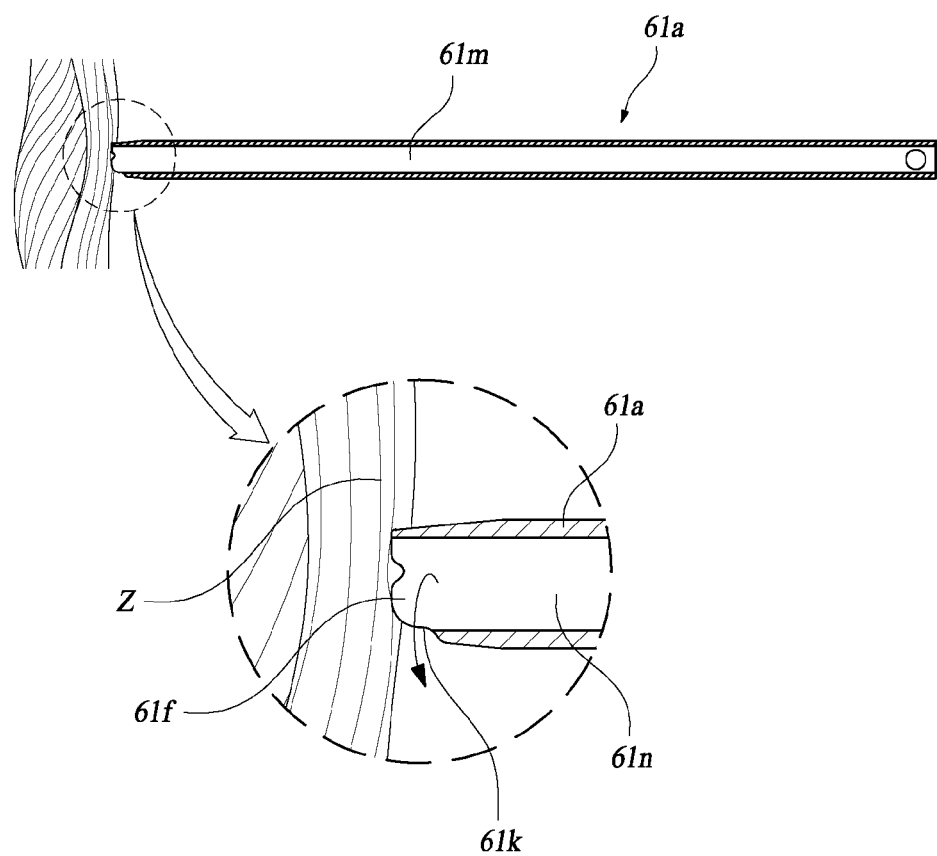
FIG. 11 is a cross-sectional view of a guide tube shown in FIG. 9.
Figure 12:
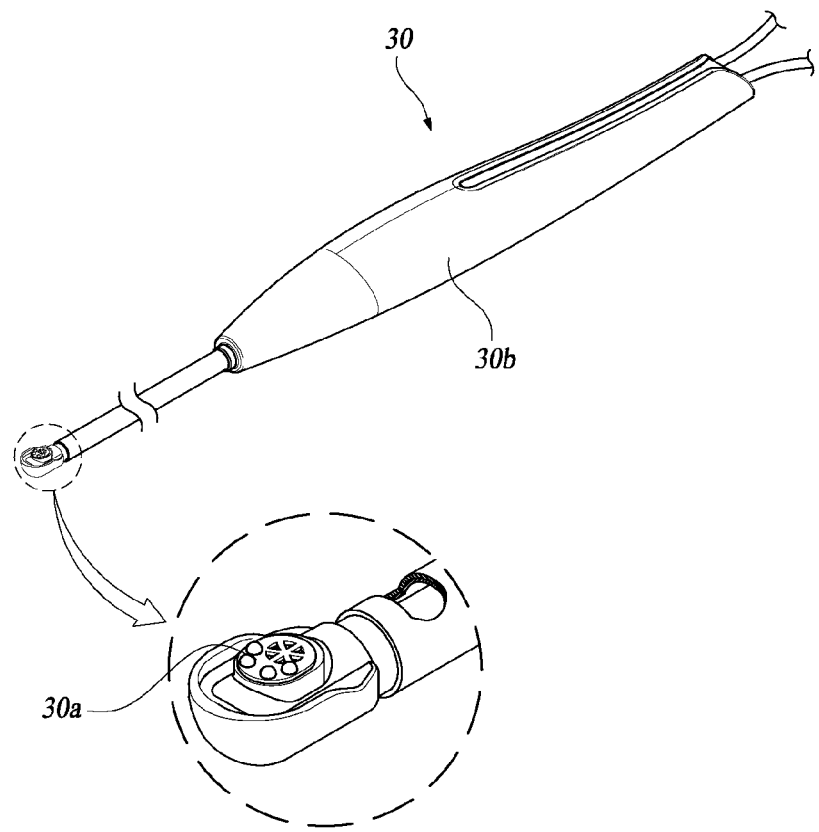
FIG. 12 is a perspective view of a radio frequency probe shown in FIG. 1.
Figure 13:
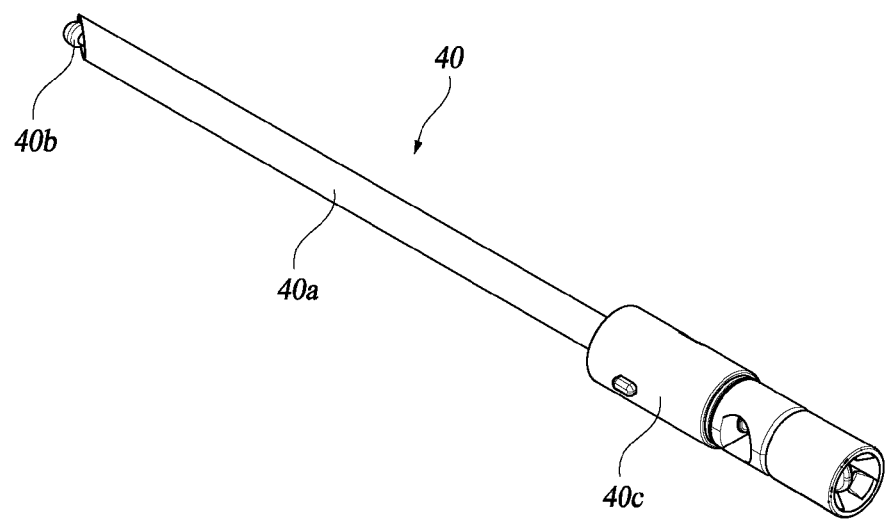
FIG. 13 is a perspective view of a shaver device shown in FIG. 1.
Figure 14:
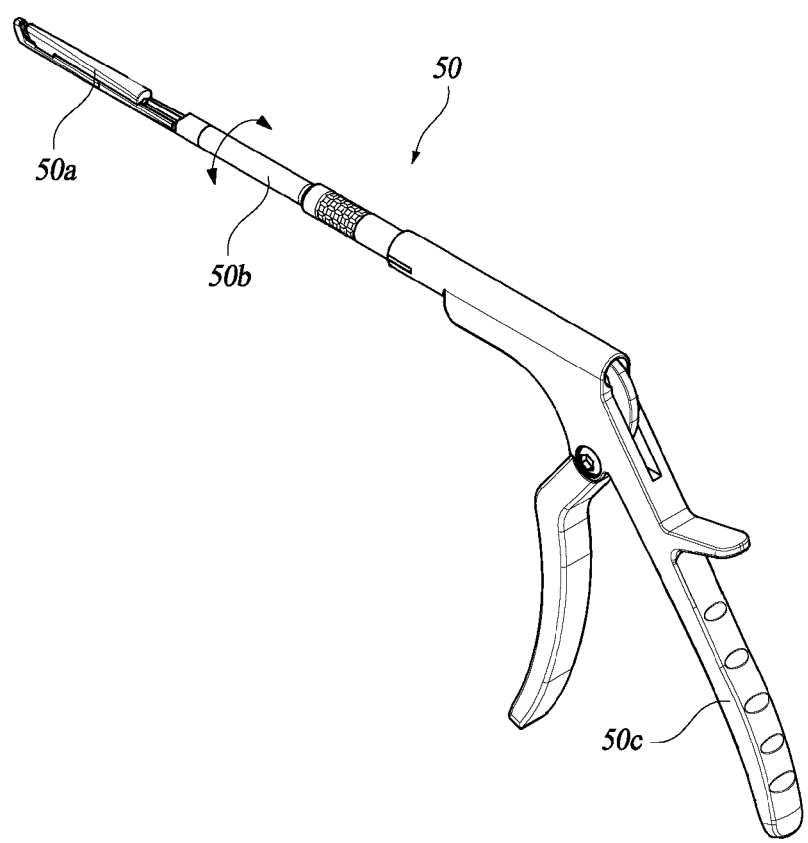
FIG. 14 is a perspective view of a K-punch shown in FIG. 1 above.

FIG. 9 is an exploded perspective view of the endoscopic device 60, and FIG. 10 is a cross-sectional view taken along line X-X of FIG. 9. In addition, FIG. 11 is a sectional view of the guide tube 61a shown in FIG. 9 above.

The endoscope 63 is a device for checking and photographing a surgical site in a patient's body, and includes: a probe 63a having flexibility, extending in the longitudinal direction, and provided with an optical cable embedded therein; a lens 63b provided at the front end of the probe 63a; and a lens barrel 63c installed at the rear end of the lens 63b.

The endoscope 63 may further include: a photographing controller for recording a video or capturing a photographed image; a light source connected to a guide cable and illuminating a photographing site; the guide cable transmitting light to the distal end of the endoscope in order to emit the light to the photographing site; and an endoscope tray for storing the endoscope and facilitating movement.

The sheath device 61 is connected to the endoscope 63 to constitute a single endoscopic device 60, and serves to support the endoscope 63 and to secure visibility during surgery. In fact, since the probe 63a of the endoscope is very thin and bends well, the lens 63b is unable to be reached a target point in the patient's body, and thus the sheath device 61 is used.

The sheath device 61 includes a guide tube 61a, a damping chamber 61m, a valve body 61b, and an adapter part 61s.

First, the guide tube 61a is extended in the longitudinal direction, is a tube-shaped member having a cavity therein, and is made of stainless steel, wherein, when being used, the front end thereof reaches a target site in the patient's body. The length of the guide tube 61a may be varied as needed. The guide tube 61a is inserted into the patient's body through the path secured by the expansion tube 11 described above.

In particular, a plurality of guide grooves 61p is formed on the inner circumference surface of the guide tube 61a. The guide groove 61p is a groove extending along the longitudinal direction of the guide tube 61a, and is a guide groove guiding the saline solution supplied from outside toward an outlet 61f.

In addition, as shown in FIG. 10, a linear protrusion 61r is formed between each of the guide grooves 61p. The linear protrusion 61r is a protrusion formed in parallel with the guide groove 61p, and a plurality of the linear protrusions is positioned in parallel to form the guide groove 61p.

The linear protrusion 61r and the guide groove 61p form a uniform interval along the circumferential direction of the guide tube 61a.

In addition, the linear protrusion 61r supports the probe 63a by partially contacting the outer circumference surface of the probe 63a inserted into a space part 61n of the guide tube 61a. The diameter of the imaginary cylinder connecting the upper end of the linear protrusion 61r is larger than the diameter of the probe 63a. Therefore, the probe 63a may move upward, downward, leftward, and rightward inside the space part 61n, and slidingly moves smoothly in the longitudinal direction.

In addition, pluralities of protrusion parts 61h and recessed parts 61g are formed at the front end of the guide tube 61a. The protrusion part 61h is a part protruding in the front end direction of the guide tube 61a, that is, in the discharge direction of the saline solution, and the recessed part 61g is a part recessed in the opposite direction thereof. In particular, in the protrusion part 61h and the recessed part 61g, a wave pattern along the circumferential direction of the guide tube 61a is repeatedly formed.

The protrusion part 61h and the recessed part 61g serve to guide the saline solution discharged from the guide tube to be flowed out in the radial direction of the guide tube. For example, when the front end of the guide tube 61a is blocked by muscles, the saline solution is allowed to be supplied through the recessed part 61g.

In addition, at a side of the front end of the guide tube 61a, a side slit 61k is formed. The side slit 61k is for controlling the flow direction of the saline solution. In other words, during biportal endoscopic spinal surgery, the flow direction of the saline solution is controlled to facilitate cleaning of the lens 63b, as the saline solution flows by gravity.

The side slit 61k also serves as a passage for the saline solution. For instance, the side slit is prepared for a case where discharge of the saline solution is difficult because even the recessed part 61g of the guide tube 61a is blocked by tissue such as muscle Z. The saline solution flowing into the inside of the guide tube 61a is discharged through the side slit 61k by the action of gravity, thereby cleaning the tissue or blood of the affected area so as to secure the visibility.

The adapter part 61s maintains a position of the endoscope 63 with respect to the sheath device 61, and is provided with a holder 61d for supporting the endoscope 63. The rear end of the guide tube 61a is opened to rearward of the holder 61d. When the probe 63a is completely inserted into inside the guide tube 61a through the holder 61d, the endoscope 63 is supported by the holder 61d and does not fall out backward.

Meanwhile, the damping chamber 61m is a space part coupled to communicate with the rear end of the guide tube 61a, and after once receiving and holding the saline solution supplied to inside thereof through the valve body 61b, transfers the saline solution to the guide tube 61a.

By applying the damping chamber 61m, a flow rate of the saline solution supplied to the guide tube 61a is kept constant. Without the damping chamber 61m, deviation in flow rate of the saline solution supplied through a saline solution supply tube 27a in FIG. 1 is directly transferred to the guide tube 61a. The deviation in the discharge flow rate of the saline solution through the outlet 61f of the guide tube 61a is severe. The capacity of the damping chamber 61m may be varied as needed.

Two valve bodies 61b are provided at positions around the damping chamber 61m, and each valve body 61b is provided with a volume control valve 61e. The volume control valve 61e is for controlling the flow rate of the saline solution passing through the valve body 61b, and is operated by a user.

The damping chamber and the valve body serve as a saline solution guide part for guiding the saline solution to the guide tube 61a.

Reference numeral 61c is an inlet to which the saline solution supply tube 27a is connected. Through the inlet 61c, the saline solution moved through the saline solution supply tube 27a reaches the affected area via the valve body 61b, the damping chamber 61m, and the guide tube 61a.

Meanwhile, the shaver device 40 is used to grind unnecessary bone parts during surgery, is provided with a handpiece 40c connected to an external wireless footswitch and provided with an operation switch (not shown), an insertion rod 40a fixed to the handpiece, and a drill burr 40b at the front end of the insertion rod.

The drill burr is a part for grinding bones, and there are various types thereof. For example, a round drill burr or a diamond drill burr may be applied. The diamond drill burr is provided with a cutting tip for cutting bones. Unlike the conventional drill bur used for endoscopic surgery, the cutting tip is embossed with an industrial diamond. Therefore, it is possible to finely adjust the depth of bone-cutting and to maximally reduce bleeding.

The cutting tip of the diamond drill burr may be implemented in a round shape as well as in other shapes such as a triangular pyramid. In addition, the diamond drill burr may further include a shield part surrounding one side of the cutting tip to cut only unnecessary parts without damaging the normal tissue part.

The radio frequency probe 30 is an instrument used to ablate soft tissue such as discs, epidural fat, and ligaments. In the case of the conventional radio frequency probe, there is a thermal damage problem in that the nerve around a surgical site is damaged to due to the tip part where the radio frequency is generated. However, the radio frequency probe 30 of the present invention includes a casing 30b, and an electrode tip 30a applying heat to the treatment site.

In addition, a power cable capable of supplying power to the radio frequency probe 30 may be further included, and a discharge tube discharging the saline solution from the patient's body to the outside may be extendedly formed on an outer side of the casing 30b.

In addition, the electrode tip 30a may be fittedly connected to the insertion rod 40a, and includes a heating part and a shield part inside thereof. A plurality of protrusions is formed on the heating part to maintain a certain distance from human body tissue, and the surrounding soft tissue is ablated with the heat output therefrom. The shield part isolates normal tissue such as nerves near the treatment site from the heating part. Therefore, it is possible to prevent normal tissue near the treatment site from being thermally damaged.

The K-punch 50 is an instrument used to tear off and remove the yellow ligament, soft tissue, and the like. The K-punch 50 includes a removal part 50a that rips out the yellow ligament or soft tissue to be removed, a shaft 50b, and a handle part 50c that supports the shaft.

The shaft may be axially rotated manually or automatically clockwise or counterclockwise. Therefore, it is possible to use the shaft by gripping at a comfortable angle regardless of the position of the tissue to be removed.

Figure 15:
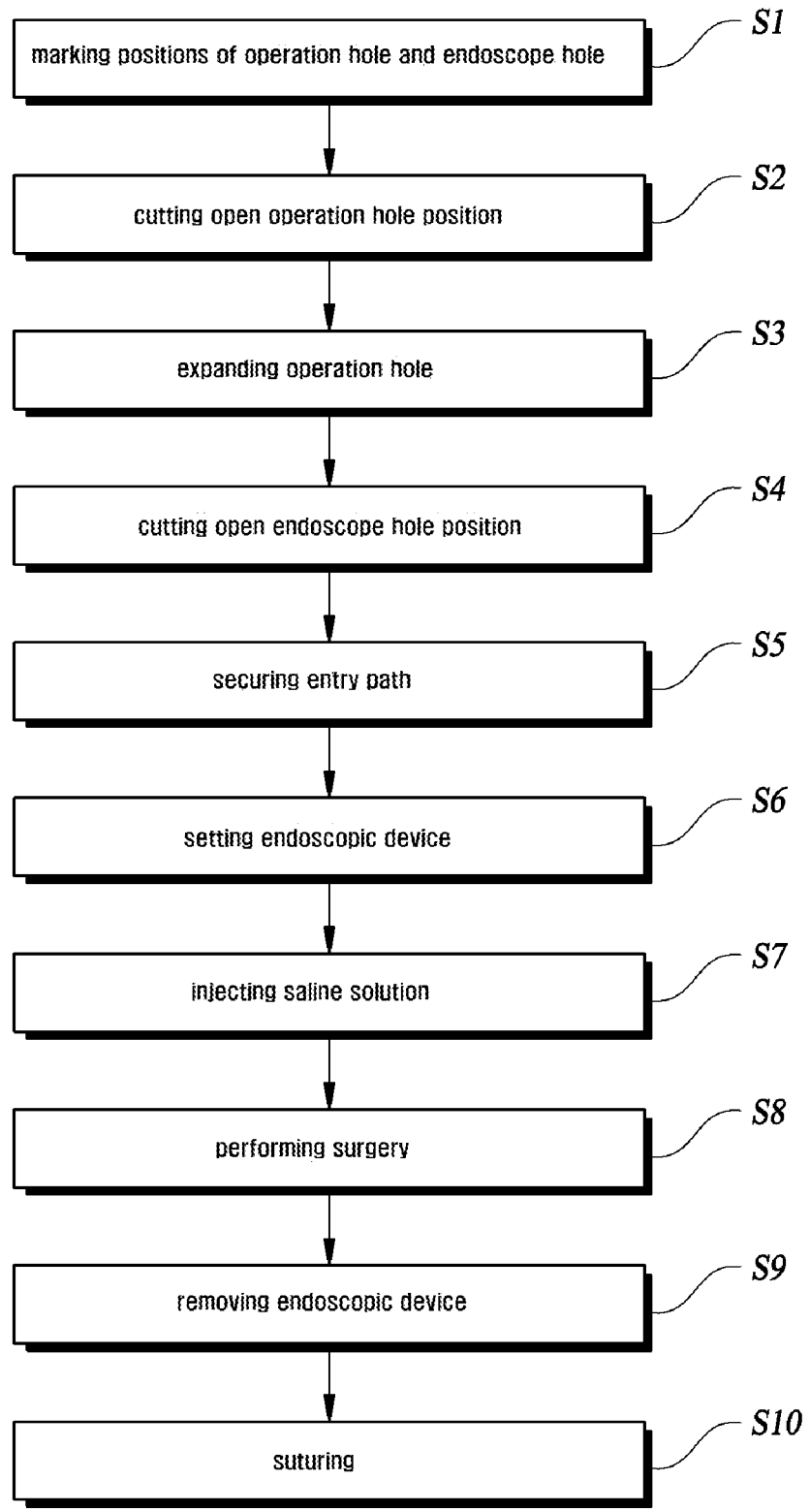
FIG. 15 is a block diagram showing a surgical method using a surgical instrument set and the endoscopic device shown in FIG. 1 as a reference.

FIG. 15 is a block diagram for explaining a method of using the endoscope 63 and the sheath device 61 in biportal endoscopic spinal surgery.

As shown, the biportal endoscopic spinal surgery includes: in a step S1, marking a position of an operation hole B and an endoscope hole A; in a step S2, cutting open a part to form the operation hole B among the marked positions; in a step S3, expanding the operation hole B by using the expansion tube 11;

in a step S4, cutting open the skin at a point to secure the endoscope hole A; in a step S5, securing an entry path to which surgical instruments are entered; in a step S6, inserting the sheath device 61 equipped with the endoscope 63 into the endoscope hole A; in a step S7, injecting the saline solution into a surgical site through the sheath; in a step S8, performing necessary surgery through the operation hole B; in a step S9, removing the sheath device 61 equipped with the endoscope from the endoscope hole A; and in a step S10, suturing the operation hole B and the endoscope hole A.

The marking the position of the operation hole B and the endoscope hole A, in the step S1, is for marking the position to be cut open to form the operation hole and the endoscope hole on the patient's skin.

In addition, the cutting open the operation hole position, in the step S2, is for making an incision part at a position vertically above a target point to the extent for inserting the expansion tube having a minimum diameter.

The expanding the operation hole B by using the expansion tube 11, in the step S3, is for securing the operation hole B by using the first expansion tube 11a to the sixth expansion tube 11f, which are described above.

In addition, the cutting open the endoscope hole A position, in the step S4, is for cutting open the position of the endoscope hole A for inserting the endoscopic device 60. The securing the entry path, in the step S5, is for separating bones and muscles by using the muscle separator 13 to secure the entry path for the surgical instruments to the surgical site and the surgical space.

The inserting the sheath device 61 equipped with the endoscope 63 into the endoscope hole A, in the step S6, is for inserting the endoscope into the sheath device before inserting into the endoscope hole.

The injecting the saline solution into the surgical site through the sheath device 61, in the step S7, is for injecting the saline solution through the inlet 61c, so as to reach the surgical site through the guide tube 61a of the sheath device.

As described above, a plurality of guide grooves 61p is formed on the inner circumference surface of the guide tube 61a, and the recessed part 61g and the protrusion part 61h, which are in the wave pattern, and the side slit 61k are also formed at the front end of the guide tube. Therefore, under the action of gravity, the saline solution flows without blockage and reaches a desired point.

The performing the surgery by inserting the surgical instruments into the operation hole B, in the step S8, is a process performed by selecting the surgical instruments such as the bilateral retractor, the muscle retractor, the suction tip, the intra disc cleaner, the cage guider, the bone chip cannula, the osteotome, the bone chip impactor, and the curved remover depending on the surgery type and the surgical situation.

The removing the endoscopic device, in the step S9, is for stopping the injection of the saline solution and extracting the endoscopic device 60 out of the endoscope hole A. The suturing, in the step S10, is for suturing the operation hole B and endoscope hole A after removing the physiological saline solution and debris remaining in the surgical space. The progress method of the biportal endoscopic spinal surgery is changed depending on the needs.

Several exemplary embodiments of the invention have been described. Nevertheless, it should be understood that the foregoing description is for illustration only and is not intended to limit the scope of the invention as defined by the following claims. Accordingly, other exemplary embodiments may also be within the scope of the technical spirit defined in the following claims. That is, those skilled in the art of the present invention may implement various modifications without departing from the scope of the present invention.

As described above, the present invention has been described in detail through specific exemplary embodiments, but the present invention is not limited to the above exemplary embodiments, and various modifications can be made by those skilled in the art within the scope of the technical spirit of the present invention.

The invention claimed is:

1. A sheath device for biportal endoscopic spinal surgery, the device comprising:
    a guide tube as a hollow tubular member extending in a longitudinal direction thereof and having a front end thereof reaching a target site in a patient's body when being used, the guide tube accommodating a probe of an endoscope inserted therein;
    a saline solution guide part mounted on a rear end of the guide tube and guiding a saline solution injected from an outside to an inside of the guide tube, the saline solution guide part comprising a valve body making the saline solution that is flowed in through an inlet to be passed through and moved to the guide tube;
    a damping chamber configured to receive and hold the saline solution once the saline solution is supplied inside the damping chamber from the valve body and prior to transferring the saline solution to the guide tube to maintain a constant flow rate of the saline solution to the guide tube;

an adapter part positioned at the rear end of the guide tube and guiding the probe of the endoscope to use to the guide tube; and a side slit to discharge the saline solution discharged from the guide tube in one direction of the guide tube is formed at a side of the front end of the guide tube.

2. The device of claim 1, wherein the saline solution guide part comprises:

a volume control valve mounted on the valve body and controlling a flow rate of the saline solution passing through the valve body.

3. The device of claim 1, wherein one or more of the valve bodies are mounted around the damping chamber to increase an amount of the saline solution supplied to the damping chamber.

4. The device of claim 1, wherein, on an inner circumference surface of the guide tube, a guide groove guiding the saline solution in the longitudinal direction of the guide tube, which is flowed into the inside of the guide tube is formed.

5. The device of claim 4, wherein a plurality of the guide grooves is disposed in parallel in a circumferential direction of the inner circumference surface of the guide tube, and a linear protrusion contacting the probe of the endoscope and supporting the probe thereof is provided between each of the guide grooves.

6. The device of claim 1, wherein the adapter part is provided with a holder maintaining a fixation state of the endoscope to the sheath device.

7. The device of claim 1, wherein, at the front end of the guide tube, protrusion parts and recessed parts are repeatedly formed in a wave pattern along the circumferential direction of the guide tube, thus guiding the saline solution discharged from the guide tube to flow out in a radial direction of the guide tube.

* * * * *